(12) United States Patent
Takamori et al.

(10) Patent No.: US 10,656,225 B2
(45) Date of Patent: May 19, 2020

(54) MAGNETIC RESONANCE IMAGING APPARATUS

(71) Applicant: Toshiba Medical Systems Corporation, Otawara-shi (JP)

(72) Inventors: Hiromitsu Takamori, Yokohama (JP); Shoji Ishizaki, Musashino (JP); Kaoru Ikeda, Yokohama (JP)

(73) Assignee: Canon Medical Systems Corporation, Otawara-shi (JP)

(*) Notice: Subject to any disclaimer, the term of this patent is extended or adjusted under 35 U.S.C. 154(b) by 198 days.

(21) Appl. No.: 15/692,295

(22) Filed: Aug. 31, 2017

(65) Prior Publication Data

US 2018/0059196 A1 Mar. 1, 2018

(30) Foreign Application Priority Data

Sep. 1, 2016 (JP) .................................. 2016-171314
Aug. 31, 2017 (JP) .................................. 2017-167010

(51) Int. Cl.
*G01R 33/385* (2006.01)
*G01R 33/34* (2006.01)
*G01R 33/36* (2006.01)
*A61B 5/055* (2006.01)

(52) U.S. Cl.
CPC .......... *G01R 33/385* (2013.01); *A61B 5/0555* (2013.01); *G01R 33/34* (2013.01); *G01R 33/36* (2013.01); *G01R 33/3854* (2013.01)

(58) Field of Classification Search
CPC ...... G01R 33/34; G01R 33/36; G01R 33/385; G01R 33/3854; A61B 5/0555
See application file for complete search history.

(56) References Cited

U.S. PATENT DOCUMENTS

| 5,144,243 A * | 9/1992 | Nakabayashi | ..... G01R 33/3415 324/318 |
| 6,029,082 A * | 2/2000 | Srinivasan | ....... G01R 33/34046 324/318 |
| 6,043,653 A * | 3/2000 | Takamori | ........... G01R 33/3854 324/300 |
| 6,954,068 B1 * | 10/2005 | Takamori | ........... G01R 33/3854 324/318 |

(Continued)

FOREIGN PATENT DOCUMENTS

| JP | 4643158 | 3/2011 |
| JP | 5280022 | 9/2013 |

(Continued)

*Primary Examiner* — Dixomara Vargas
(74) *Attorney, Agent, or Firm* — Oblon, McClelland, Maier & Neustadt, L.L.P.

(57) ABSTRACT

A magnetic resonance imaging apparatus according to an embodiment includes a static magnetic field magnet, a gradient coil, a space forming structure, a magnet supporting member, and a space forming structure supporter. The gradient coil is provided on an inner circumferential side of the static magnetic field magnet. The space forming structure forms a patient space on an inner circumferential side of the gradient coil. The magnet supporting member supports the static magnetic field magnet on a floor surface. The space forming structure supporter is attached to the magnet supporting member and supports the space forming structure.

22 Claims, 9 Drawing Sheets

(56) References Cited

U.S. PATENT DOCUMENTS

| | | | | |
|---|---|---|---|---|
| 7,525,311 B2* | 4/2009 | Steckner | ............ | G01R 33/3415 324/318 |
| 7,755,359 B2* | 7/2010 | Yamamizu | ............ | A61B 5/055 324/320 |
| 2008/0164875 A1* | 7/2008 | Haworth | ................ | G01R 33/28 324/318 |
| 2008/0211495 A1* | 9/2008 | Steckner | ............ | G01R 33/3415 324/300 |
| 2008/0265887 A1* | 10/2008 | Linz | ........................ | G01R 33/28 324/318 |
| 2008/0309343 A1* | 12/2008 | Yamamizu | ............ | A61B 5/055 324/320 |
| 2012/0169341 A1* | 7/2012 | McKinnon | ............ | A61B 6/037 324/318 |
| 2012/0245453 A1* | 9/2012 | Tryggestad | ............ | A61B 6/463 600/413 |
| 2014/0292335 A1* | 10/2014 | Kachi | ................ | G01R 33/246 324/309 |
| 2015/0025358 A1* | 1/2015 | Emaci | ................ | A61B 5/0035 600/411 |
| 2015/0087966 A1* | 3/2015 | Anderson | ............ | A61B 5/0002 600/415 |
| 2015/0145516 A1 | 5/2015 | Ueda et al. | | |
| 2015/0355300 A1* | 12/2015 | Ooshima | ............ | G01R 33/5608 324/309 |
| 2017/0287113 A1* | 10/2017 | Dwivedi | ................ | G06T 7/11 |
| 2018/0028092 A1* | 2/2018 | Okamoto | ............ | A61B 5/0035 |
| 2018/0064365 A1* | 3/2018 | Srinivasan | ............ | A61G 11/00 |
| 2018/0120395 A1* | 5/2018 | Saha | .................... | G01R 33/422 |

FOREIGN PATENT DOCUMENTS

| | | |
|---|---|---|
| JP | 2015-119953 | 7/2015 |
| WO | WO 2006/062028 A1 | 6/2006 |

* cited by examiner

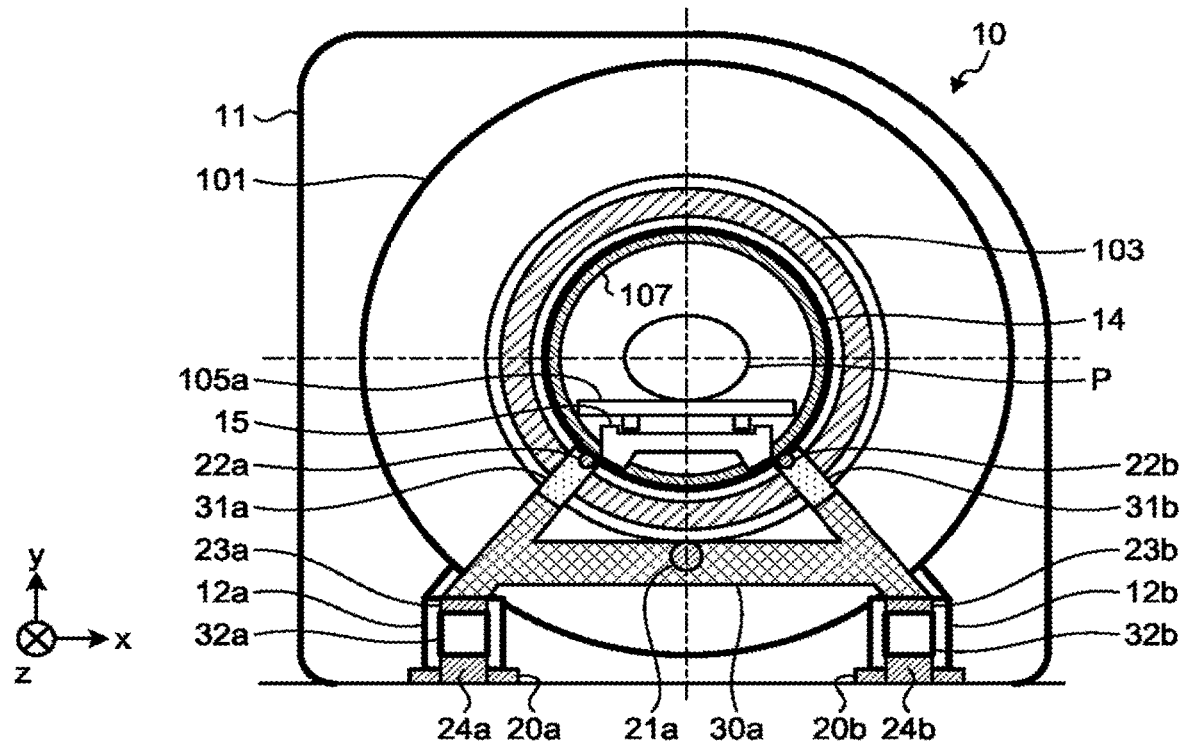
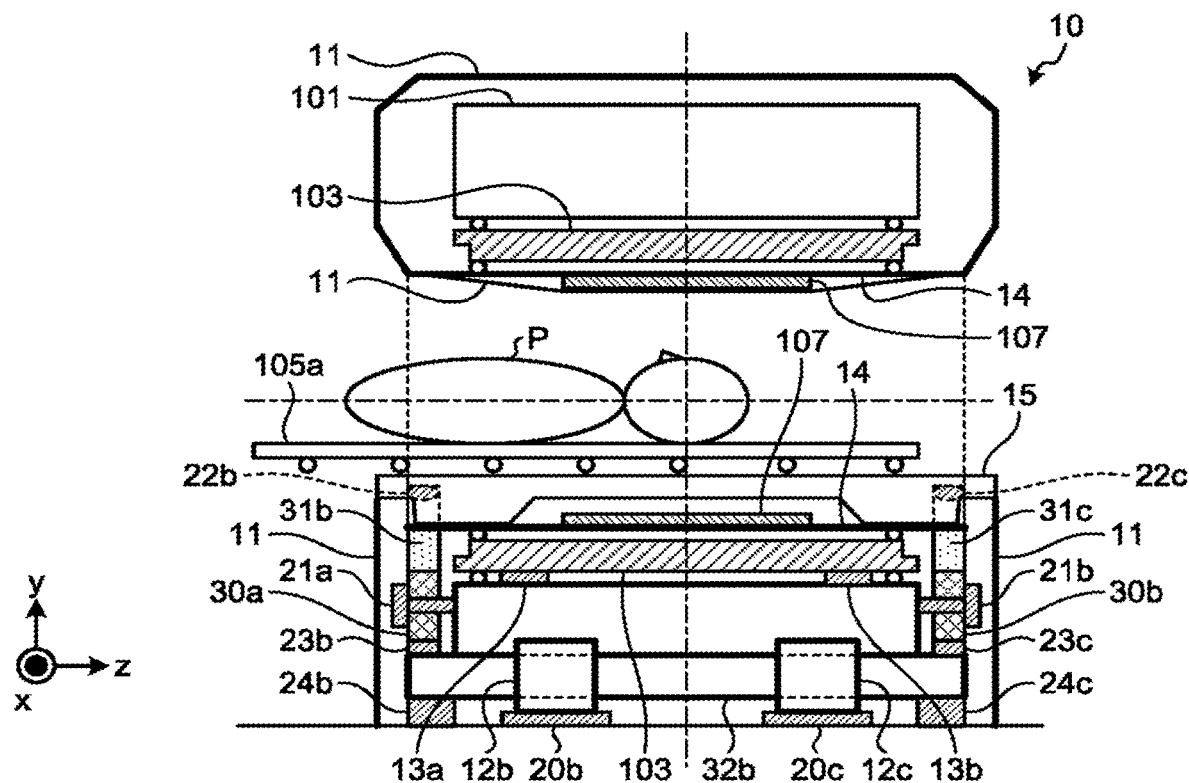

MAGNETIC RESONANCE IMAGING APPARATUS

CROSS-REFERENCE TO RELATED APPLICATIONS

This application is based upon and claims the benefit of priority from Japanese Patent Application No. 2016-171314, filed on Sep. 1, 2016 and Japanese Patent Application No. 2017-167010, filed on Aug. 31, 2017; the entire contents of which are incorporated herein by reference.

FIELD

Embodiments described herein relate generally to a magnetic resonance imaging apparatus.

BACKGROUND

Conventionally, various noise reduction technologies for reducing the sound (noise) generated from a gradient coil in a magnetic resonance imaging (MRI) apparatus have been proposed.

Sound generated from a gradient coil includes air propagation sound that is sound transmitted via the surrounding air serving as a medium and solid propagation sound that is sound transmitted via a solid that the sound contacts and that serves as a medium. For example, a technology of reducing the air propagation sound by arranging a gradient coil in an airtight container to cause the surrounding space in the airtight container to be a vacuum is known. Furthermore, for example, the solid propagation sound is reduced by insulating a bore tube that forms a patient space (also referred to as "bore") and a gradient coil from each other with a vibration absorbing material.

BRIEF DESCRIPTION OF THE DRAWINGS

FIG. 2 is a diagram for explaining a configuration of a gantry of the MRI apparatus according to the embodiment;

FIG. 3 is a diagram for explaining the configuration of the gantry of the MRI apparatus according to the embodiment;

DETAILED DESCRIPTION

An objective of the present embodiment is to provide a magnetic resonance imaging apparatus enabling reduction of solid propagation sound caused by a gradient coil.

A magnetic resonance imaging apparatus according to an embodiment includes a static magnetic field magnet, a gradient coil, a space forming structure, a magnet supporting member, and a space forming structure supporter. The gradient coil is provided on an inner circumferential side of the static magnetic field magnet. The space forming structure forms a patient space on an inner circumferential side of the gradient coil. The magnet supporting member supports the static magnet on a floor surface. The space forming structure supporter is attached to the magnet supporting member and supports the space forming structure.

The magnetic resonance imaging apparatus according to the embodiment will be described with reference to the accompanying drawings.

Embodiment

Figure 1:
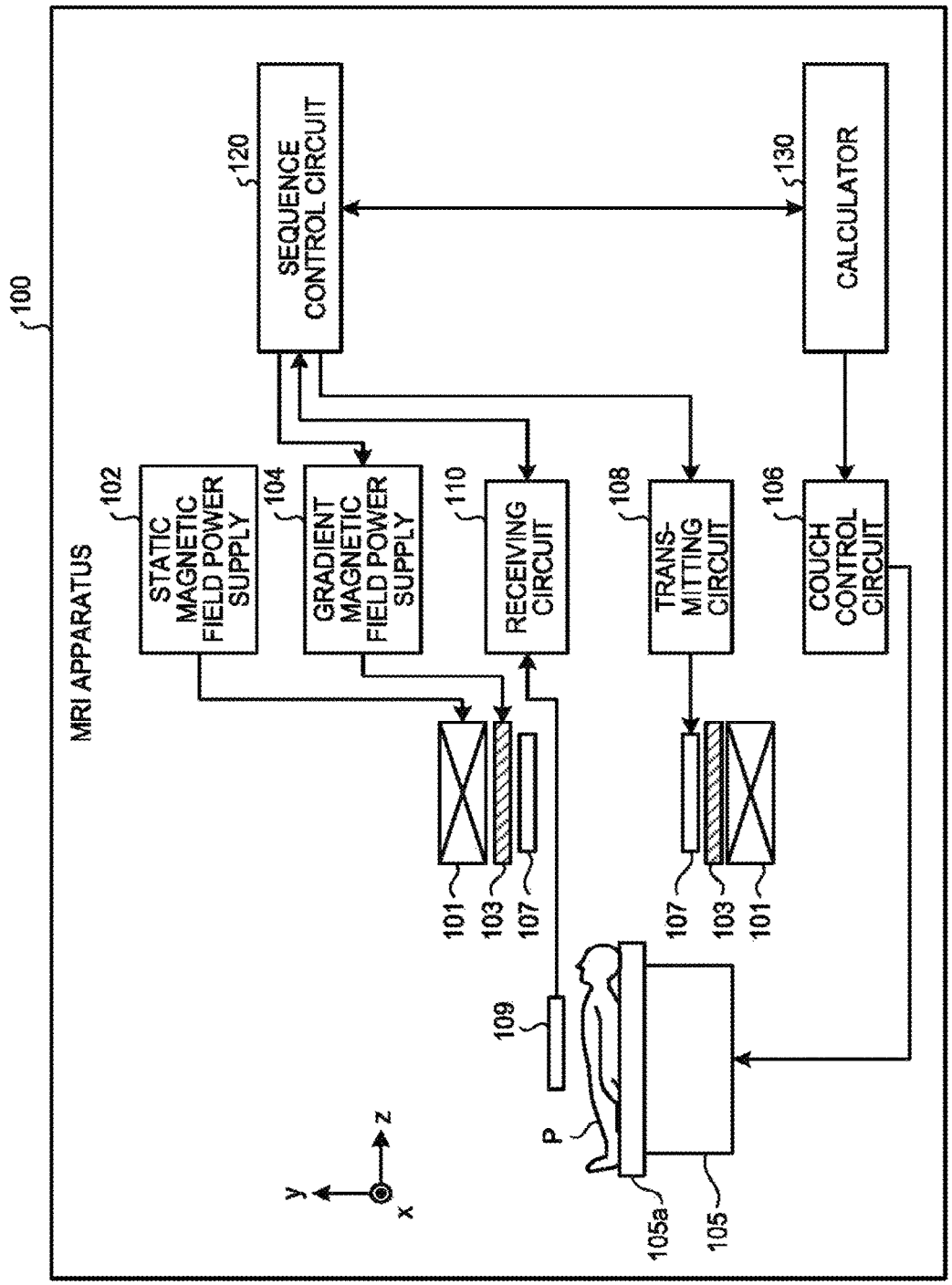
FIG. 1 is a block diagram illustrating a configuration of an MRI apparatus according to an embodiment.

FIG. 1 is a block diagram illustrating a configuration of an MRI apparatus 100 according to an embodiment. The magnetic resonance imaging apparatus will be referred to as the MRI apparatus 100 below.

As illustrated in FIG. 1, the MRI apparatus 100 includes a static magnetic field magnet 101, a static magnetic field power supply 102, a gradient coil 103, a gradient magnetic field power supply 104, a couch 105, a couch control circuit 106, a whole body (WB) coil 107, a transmitting circuit 108, a receiving coil 109, a receiving circuit 110, a sequence control circuit 120, and a calculator 130. The MRI apparatus 100 does not include a subject P (such as a human body). The configuration illustrated in FIG. 1 is an example only and thus the embodiments are not limited to the configuration illustrated in FIG. 1.

The static magnetic field magnet 101 is a magnet that is formed into a hollow and approximately cylindrical shape and generates a static magnetic field in its internal space. The static magnetic field magnet 101 is, for example, a superconducting magnet that is supplied with a current from the static magnetic field power supply 102 and is thus excited. The static magnetic field power supply 102 supplies an electric current to the static magnetic field magnet 101. The static magnetic field magnet 101 may be a permanent magnet. In this case, the MRI apparatus 100 does not necessarily include the static magnetic field power supply 102. The static magnetic field power supply 102 may be provided independently of the MRI apparatus 100. The approximately cylindrical shape includes, in addition to a cylindrical shape of a true circle, a cylindrical shape of a deformed oval that does not significantly impair the function of the MRI apparatus 100.

The gradient coil 103 is a coil structure that is formed into a hollow and approximately cylindrical shape and is arranged on the inner side of the static magnetic field magnet 101. The gradient coil 103 is formed by combining three coils corresponding to x, y and z axes that are orthogonal with one another. The three coils are individually supplied with currents from the gradient magnetic field power supply 104 and generate gradient magnetic fields whose magnetic field intensities vary along the x, y and z axes, respectively. The gradient magnetic fields corresponding to the x, y and z axes are, for example, a slice encoding gradient magnetic field $G_{SE}$ (or a slice selecting gradient magnetic field $G_{SS}$), a phase encoding gradient magnetic field $G_{PE}$, and a frequency encoding gradient magnetic field $G_{RO}$. The gradient coil 103 is formed by impregnating the three coils with, for example, an epoxy resin. The gradient magnetic field power supply 104 supplies a current to the gradient coil 103.

The couch 105 includes a couchtop 105a on which the subject P is placed. Under the control of the couch control circuit 106, the couch 105 inserts the couchtop 105a on which the subject P is kept placed into the hollow (imaging entrance) of the gradient coil 103. Normally, the couch 105 is set such that its longitudinal direction is parallel with the center axis of the static magnetic field magnet 101. Under the control of the calculator 130, the couch control circuit 106 drives the couch 105 to move the couchtop 105a in the longitudinal direction and vertically.

The WB coil 107 is arranged on the inner side of the gradient coil 103. The WB coil 107 is supplied with an RF pulse from the transmitting circuit 108 and thus generates a high-frequency magnetic field. Furthermore, the WB coil 107 receives a magnetic resonance signal (hereinafter, "magnetic resonance (MR) signal" as appropriate) and outputs the received MR signal to the receiving circuit 110.

The transmitting circuit 108 supplies, to the WB coil 107, an RF pulse corresponding to a Larmor frequency that is determined according to the type of atom to be dealt with and the magnetic field intensity.

The receiving coil 109 is arranged on the inner side of the gradient coil 103 and receives the MR signal that is emitted from the subject P because of the effect of the high-frequency magnetic field. On receiving the MR signal, the receiving coil 109 outputs the received MR signal to the receiving circuit 110.

The WB coil 107 and the receiving coil 109 are examples only and the embodiments are not limited thereto. For example, the receiving coil 109 is not necessarily provided. It suffices if the WB coil 107 and the receiving coil 109 consist of one of or a combination of a coil having only a transmitting function, a coil having only a receiving function and a coil having the transmitting and receiving functions.

The receiving circuit 110 detects the MR signal that is output from the receiving coil 109 and generates MR data based on the detected MR signal. Specifically, the receiving circuit 110 generates MR data by converting the MR signal, which is output from the receiving coil 109, into a digital signal. The receiving circuit 110 transmits the generated MR data to the sequence control circuit 120.

The sequence control circuit 120 images the subject P by driving the gradient magnetic field power supply 104, the transmitting circuit 108 and the receiving circuit 110 according to sequence information that is transmitted from the calculator 130. The sequence information is information that defines a procedure to perform imaging. The sequence information defines an intensity of a current to be supplied to the gradient coil 103, a timing at which the current is supplied, an intensity of an RF pulse supplied by the transmitting circuit 108 to the gradient coil 103, a timing at which the RF pulse is supplied, and a timing at which the receiving circuit 110 detects the MR signal. For example, the sequence control circuit 120 is an integrated circuit, such as an application specific integrated circuit (ASIC) or a field programmable gate array (FPGA), or an electronic device, such as a central processing unit (CPU) or a micro processing unit (MPU).

Once the sequence control circuit 120 receives the MR signal data from the receiving circuit 110 as a result of imaging the subject P by controlling the gradient magnetic field power supply 104, the transmitting circuit 108, and the receiving circuit 110, the sequence control circuit 120 transfers the received MR signal data to the calculator 130.

The calculator 130, for example, controls the entire MRI apparatus 100 and generates MR images. For example, the calculator 130 causes the sequence control circuit 120 to execute an imaging sequence according to imaging conditions that are input by an operator. The calculator 130 reconstructs an image based on the MR signal data that is transmitted from the sequence control circuit 120. The calculator 130 stores the reconstructed image in the storage unit and displays the reconstructed image on a display unit. The calculator 130 is, for example, an information processing device, such as a computer.

The MRI apparatus 100 according to the embodiment configured as described above reduces the solid propagation sound caused by the gradient coil 103.

Vibrations of the gradient coil 103 propagate via a solid serving as a medium and are converted into air vibrations and thus are transmitted to the subject P. In other words, reducing the vibrations propagating from the gradient coil 103 (also referred to as "solid propagation vibrations") is equivalent to reducing the solid propagation sound.

To deal with this, the MRI apparatus 100 according to the embodiment supports a bore tube 14 with a bore tube supporting structure originating on magnet legs (magnet legs 12a to 12d to be described below) that support the static magnetic field magnet 101. This causes the solid propagation vibrations caused by the gradient coil 103 to propagate to the bore tube 14 via (around) the magnet legs and thus the solid propagation vibrations attenuate (reduce) according to the distance of a propagation route. Accordingly, the MRI apparatus 100 is able to reduce the solid propagation sound (solid propagation vibrations) caused by the gradient coil 103.

In the following embodiment, a configuration for reducing the solid propagation sound (solid propagation vibrations) will be described; however, the embodiments are not limited thereto. For example, the MRI apparatus 100 may have a configuration for reducing the air propagation sound in addition to the following configuration. Any conventional noise reduction technology, such as a technology of vacuuming an airtight container in which the gradient coil 103 is housed or a technology of shielding air propagation by using an acoustic absorbent or an acoustic insulator, may be used together for the configuration for reducing the air propagation sound. In other words, using the configuration of the following embodiment to be described below and the conventional noise reduction technology together makes it possible to reduce the solid propagation sound remaining in the conventional technology.

FIGS. 2 and 3 are diagrams for explaining a configuration of a gantry 10 of the MRI apparatus 100 according to the embodiment. FIG. 2 exemplifies the diagram of the internal structure of the gantry 10 viewed from its axial direction. FIG. 3 exemplifies a cross sectional view along a y-z plane passing through the center axis of the static magnetic field magnet 101. The content of FIGS. 2 and 3 is an example only and the embodiments are not limited to the example illustrated in FIGS. 2 and 3.

As illustrated in FIGS. 2 and 3, the gantry 10 includes, for example, an approximately cylindrical space (bore) in which the subject P is placed and that is surrounded by a gantry cover 11. The static magnetic field magnet 101 and the gradient coil 103 each having an approximately cylindrical shape are set in the gantry 10.

The static magnetic field magnet 101 is supported by the magnet leg 12a, a magnet leg 12b, a magnet leg 12c and a magnet leg 12d (not illustrated in the drawings) from a floor surface. Although not illustrated in the drawings, the magnet leg 12d is arranged in a symmetrical position to that of the magnet leg 12c with respect to the y-z plane.

Each of the magnet legs 12a to 12d support the static magnetic field magnet 101 on the floor surface. For example, the magnet legs 12a to 12d are set between the outer circumferential surface of the static magnetic field magnet 101 and the floor surface on both sides with respect to the axial direction of the static magnetic field magnet 101. In the example illustrated in the drawings, the magnet legs 12a to 12d are arranged in symmetrical positions with respect to the y-z plane. In other words, the magnet legs 12a to 12d are arranged on the floor surface and in symmetrical positions with respect to the axial direction. The arrangement of the magnet legs 12a to 12d are not limited to the example illustrated in the drawings. For example, it suffices if at least one of the magnet legs 12a to 12d be arranged in each of the two spaces that are between the static magnetic field magnet 101 and the floor surface and that are sectioned by the y-z plan. The magnet legs 12a to 12d are not necessarily arranged in symmetrical positions with respect to the y-z plane.

Vibration absorbing members 20a to 20d are arranged between the magnet legs 12a to 12d and the floor surface. Specifically, the vibration absorbing member 20a is arranged between the magnet leg 12a and the floor surface. The vibration absorbing member 20b is arranged between the magnet leg 12b and the floor surface. The vibration absorbing member 20c is arranged between the magnet leg 12c and the floor surface. The vibration absorbing member 20d is arranged between the magnet leg 12d and the floor surface.

In order to reduce vibrations of the gantry 10 while supporting the weight of the gantry 10, each of the vibration absorbing members 20a to 20d is formed of a vibration absorbing material, such as rubber or elastomer. Each of the vibration absorbing members 20a to 20d is an exemplary magnet supporting member. In the following descriptions, vibration absorbing materials are collectively referred to as a "vibration absorbing material" and members formed by, for example, molding the vibration absorbing material are referred to as a "vibration absorbing member".

The gradient coil 103 is supported by a coil supporting member 13a and a coil supporting member 13b in the internal space of the static magnetic field magnet 101. The coil supporting member 13a and the coil supporting member 13b are formed of, for example, a vibration absorbing material, such as rubber or elastomer, in order to support the weight of the gradient coil 103 while reducing the vibrations of the gradient coil 103.

Furthermore, the bore tube 14 that forms the bore (space) in which the subject P is placed is arranged in the internal space of the gradient coil 103. The WB coil 107 and a couch rail 15 are set in the bore tube 14. The couch rail 15 is a rail for inserting the couchtop 105a on which the subject P is kept placed into the bore.

The bore tube 14 is supported by a bore tube supporting structure originating on the magnet legs 12a to 12d. The bore tube supporting structure is attached to the magnet legs 12a to 12d to support the bore tube 14. The bore tube supporting structure is formed of a front frame, a back frame, and a bottom frame.

The front frame is a supporting member that supports an end of the bore tube 14 on the side of the couch (the side on which there is the couch 105). The front frame is formed of a supporting member 30a, a supporting member 31a, and a supporting member 31b.

The back frame is a supporting member that supports the end of the bore tube 14 on the counter side of the couch (the side opposite to the couch). The back frame is formed of a supporting member 30b, a supporting member 31c, and a supporting member 31d (not illustrated in the drawings).

Although not illustrated in the drawings, the supporting member 31d is arranged in a symmetrical position to the position of the supporting member 31c with respect to the y-z plane.

The bottom frame that is a long member (beam) longer than the length of the static magnetic field magnet 101 in its axial direction and that is a supporting member that supports the front frame and the back frame at both ends in the axial direction. The bottom frame includes a supporting member 32a and a supporting member 32b. The supporting member 32a is supported by the magnet legs 12a and 12d. The supporting member 32b is supported by the magnet legs 12b and 12c.

As described above, in the MRI apparatus 100 according to the embodiment, the bottom frame is a member longer than the length of the static magnetic field magnet 101 in its axial direction and is attached to the magnet legs. The front frame supports the end of the bore tube 14 at the end of the bottom frame on the side of the couch. The bottom frame supports the end of the bore tube 14 at the end of the bottom frame on the counter side of the couch. Accordingly, the MRI apparatus 100 is able to reduce the solid propagation sound (solid propagation vibrations) caused by the gradient coil 103.

For example, in the MRI apparatus 100 according to the embodiment, the solid propagation vibrations caused by the gradient coil 103 propagate to the static magnetic field magnet 101 via the coil supporting members 13a and 13b and then transmitted to the magnet legs 12a to 12d. The solid propagation vibrations then propagate to the front frame and the back frame via the bottom frame from the magnet legs 12a to 12d and are transmitted to the bore tube 14. In other words, the solid propagation vibrations caused by the gradient coil 103 propagate to the bore tube 14 via the magnet legs 12a to 12d. Accordingly, for example, compared to the case where the vibrations propagate not via the magnet legs 12a to 12d, the route of propagation of the solid propagation vibrations is long. For this reason, the MRI apparatus 100 according to the embodiment is able to attenuate (reduce) the solid propagation vibrations caused by the gradient coil 103 according to the length of the propagation route.

The supporting members 30a and 30b are set on both ends of the bottom frame (the supporting members 32a and 32b). The supporting members 30a and 30b are attached to the end faces of the static magnetic field magnet 101. In the example illustrated in the drawings, the supporting member 30a is attached to the end face of the static magnetic field magnet 101 on the side of the couch via a vibration absorbing member 21a. The supporting member 30b is attached to the end face of the static magnetic field magnet 101 on the counter side of the couch via a vibration absorbing member 21b. The vibration absorbing members 21a and 21b are formed of, for example, a vibration mitigation alloy (a vibration absorbing alloy). For the vibration mitigation alloy, any vibration mitigation alloy, such as a dislocation vibration mitigation alloy or a bicrystal alloy, may be used. Alternatively, for example, the vibration absorbing members 21a and 21b may be formed of a vibration absorbing alloy, such as rubber or elastomer, instead of vibration mitigation alloys.

The supporting members 30a and 30b are attached to the end faces of the static magnetic field magnet 101 in order to inhibit the motion (sway) of the bore tube 14 (and the WB coil 107) in its axial direction. Specifically, the vibration absorbing member 21a inhibits the motion in the positive direction of the z direction and inhibits the motion in the negative direction of the z direction. Accordingly, it is possible to inhibit image degradation due a change in the positional relation between an RF shield that is set in the gradient coil 103 and the WB coil 107. With respect to the example illustrated in the drawings, the case where the supporting members 30a and 30b are attached to the end faces of the static magnetic field magnet 101, respectively; however, the embodiments are not limited thereto. For example, if it is possible to inhibit the motion of the bore tube 14 in the axial direction, it suffices if any one of the supporting members 30a and 30b is attached to the end face of the static magnetic field magnet 101. In other words, it suffices if any one of the supporting members 30a and 30b is attached to the end face of the static magnetic field magnet 101 via the vibration absorbing member 21a and/or the vibration absorbing member 21b. The case where any one of the supporting members 30a and 30b is attached to the end face of the static magnetic field magnet 101 will be described below.

The supporting member 30a is adhered to each of the supporting members 31a and 31b with an elastic adhesive. The supporting member 30b is adhered to each of the supporting member 31c and the supporting member 31d with the elastic adhesive. The elastic adhesive is an adhesive in which the hardened material servers as an elastic body. The elastic adhesive is, for example, a silicone, modified silicone or urethane adhesive. Accordingly, the effect of attenuating vibrations (dumping effect) in the front frame and the back frame is enhanced and thus it is possible to reduce the solid propagation sound.

The supporting members 31a to 31d support the ends of the bore tube 14 via each of vibration absorbing members 22a to 22d. Each of the vibration absorbing members 22a to 22d is formed of a vibration absorbing material, such as rubber or elastomer. According to the example illustrated in the drawings, the supporting member 31a supports the end of the bore tube 14 on the side of the couch via the vibration absorbing member 22a. The supporting member 31b supports the end of the bore tube 14 on the side of the couch via the vibration absorbing member 22b. The supporting member 31c supports the end of the bore tube 14 on the counter side of the couch via the vibration absorbing member 22c. The supporting member 31d supports the end of the bore tube 14 on the counter side of the couch via the vibration absorbing member 22d. Although not illustrated in the drawings, the vibration absorbing member 22d is arranged in a position symmetrical to the position of the vibration absorbing member 22c with respect to the y-z plane.

Each of the supporting members 31a to 30d is formed of a material, such as plastic or stainless steel (SUS316 according to the JIS standards) because there is a possibility that the member corresponding to the inner area of the static magnetic field magnet 101 is influenced by the gradient magnetic field leaked from the gradient coil 103.

In other words, there is a possibility that the gradient magnetic field leaks from both ends of the gradient coil 103 in the z direction, an eddy current thus occurs in a material having conductivity or magnetism, and the material vibrates accordingly. For this reason, the material of the member corresponding to the internal area of the static magnetic field magnet 101 in the z direction is preferably a material having a property of at least any one of non-conductivity and non-magnetism. Each of the supporting members 31a to 31d is not limited to plastic or stainless steel. Each of the supporting members 31a to 31d may be formed of any material having a property of at least any one of non-conductivity and non-magnetism. In addition to the supporting members 31a to 31d, members corresponding to the inner area of the static magnetic field magnet 101 among the members forming the front frame and the back frame are preferably formed of a material having a property of at least any one of non-conductivity and non-magnetism. In other words, members in positions corresponding to the area whose x-coordinate and y-coordinate are covered by the inner diameter of the static magnetic field magnet 101 are preferably formed of a material having a property of at least any one of non-conductivity and non-magnetism.

The supporting members 30a and 30b and the supporting members 31a to 31d are formed to be hollow and the formed hollow area is filled with a vibration-absorbing gel material. For the vibration-absorbing gel material, a vibration-absorbing gel material, such as silicone gel or urethane gel, is used; however, the embodiments are not limited thereto, and any gel (or jelly) material is usable. Accordingly, the effect of attenuating vibrations in the supporting members 30a and 30b and the supporting members 31a to 31d is enhanced and thus it is possible to reduce the solid propagation sound.

The supporting members 32a and 32b are members longer than the length of the static magnetic field magnet 101 in its axial direction and are supported by the magnet legs 12a to 12d. In the example illustrated in the drawings, the supporting member 32a is supported such that the supporting member 32a penetrates through the magnet legs 12a and 12d in its axial direction. The supporting member 32b is supported such that the supporting member 32b penetrates through the magnet legs 12b and 12c in its axial direction. Each of the supporting members 32a and 32b is formed to be hollow. Accordingly, it is possible to attach a jig for conveying the gantry 10 in the formed hollow area (hollow) of each of the supporting members 32a and 32b. When the jig for the conveying is attached, the supporting members 32a and 32b are preferably set in symmetrical positions with respect to the y-z plane.

The supporting members 32a and 32b support the front frame and the back frame via vibration absorbing members 23a to 23d. Each of the vibration absorbing members 23a to 23d is formed of a vibration absorbing material, such as rubber or elastomer. In the example illustrated in the drawings, the supporting member 32a supports the supporting member 30a via the vibration absorbing member 23a. The supporting member 32a supports the supporting member 30b via the vibration absorbing member 23d (not illustrated in the drawings). The supporting member 32b supports the supporting member 30a via the vibration absorbing member 23b. The supporting member 32b supports the supporting member 30b via the vibration absorbing member 23c. Although not illustrated in the drawings, the vibration absorbing member 23d is arranged in a position symmetrical to the position of the vibration absorbing member 23c with respect to the y-z plane.

The vibration absorbing member 23a is formed of a vibration absorbing material having a spring constant different from that of the vibration absorbing member 23d. The vibration absorbing member 23b is formed of a vibration absorbing material having a spring constant different from that of the vibration absorbing member 23c. In other words, the spring constant of the vibration absorbing members 23a and 23b that are set on the bottom surface of the front frame is different from that of the vibration absorbing members 23c and 23d that are set on the bottom surface of the back frame. This is for changing the condition on sympathetic vibration of the bore tube 14 by setting different sprint constants between the front frame and the back frame corresponding to the propagation route of the solid propagation vibrations to the bore tube 14 and thus for preventing sympathetic vibrations in the bore tube 14.

Vibration absorbing members 24a to 24d are arranged between both ends of the bottom frame in its axial direction and the floor surface. In the example illustrated in the drawings, the vibration absorbing member 24a is arranged between the end of the supporting member 32a on the side of the couch and the floor surface. The vibration absorbing member 24d is arranged between the end of the supporting member 32a on the counter side of the couch and the floor surface. The vibration absorbing member 24b is arranged between the end of the supporting member 32b on the side of the couch and the floor surface. The vibration absorbing member 24c is arranged between the end of the supporting member 32b on the side of the couch and the floor surface.

Although not illustrated in the drawings, the vibration absorbing member 24d is arranged in a position symmetrical to the position of the vibration absorbing member 24c with respect to the y-z plane.

The vibration absorbing members 24a to 24d are formed of a vibration absorbing material having a spring constant different from that of the vibration absorbing members 20a to 20d. In other words, the spring constant of the vibration absorbing members 24a to 24d that are set on the bottom surface of the bottom frame is different from the spring constant of the vibration absorbing members 20a to 20d that are set on the bottom surface of the magnet legs 12a to 12d.

This is for preventing sympathetic vibration of the bottom frame due to the solid propagation vibrations transmitted between the bottom frame and the floor surface.

As described above, in the MRI apparatus 100 according to the embodiment, the bore tube 14 is supported by the structure originating on the magnet legs 12a to 12d. In other words, in the MRI apparatus 100, the solid propagation vibrations caused by the gradient coil 103 propagate to the bore tube 14 via the magnet legs 12a to 12d. Accordingly, for example, compared to the case where the solid propagation vibrations propagate not via the magnet legs 12a to 12d, the propagation route of the solid propagation vibrations is long. For example, compared to the case where the solid propagation vibrations propagate from an airtight container in which the gradient coil 103 is housed to the bore tube 14 or the case where the solid propagation vibrations propagate from the end faces of the static magnetic field magnet 101 to the bore tube 14 via the supporting members, the propagation route of the solid propagation vibrations is long. The MRI apparatus 100 according to the embodiment is thus able to attenuate (reduce) the solid propagation vibrations caused by the gradient coil 103 according to the length of the propagation route.

Figure 4:
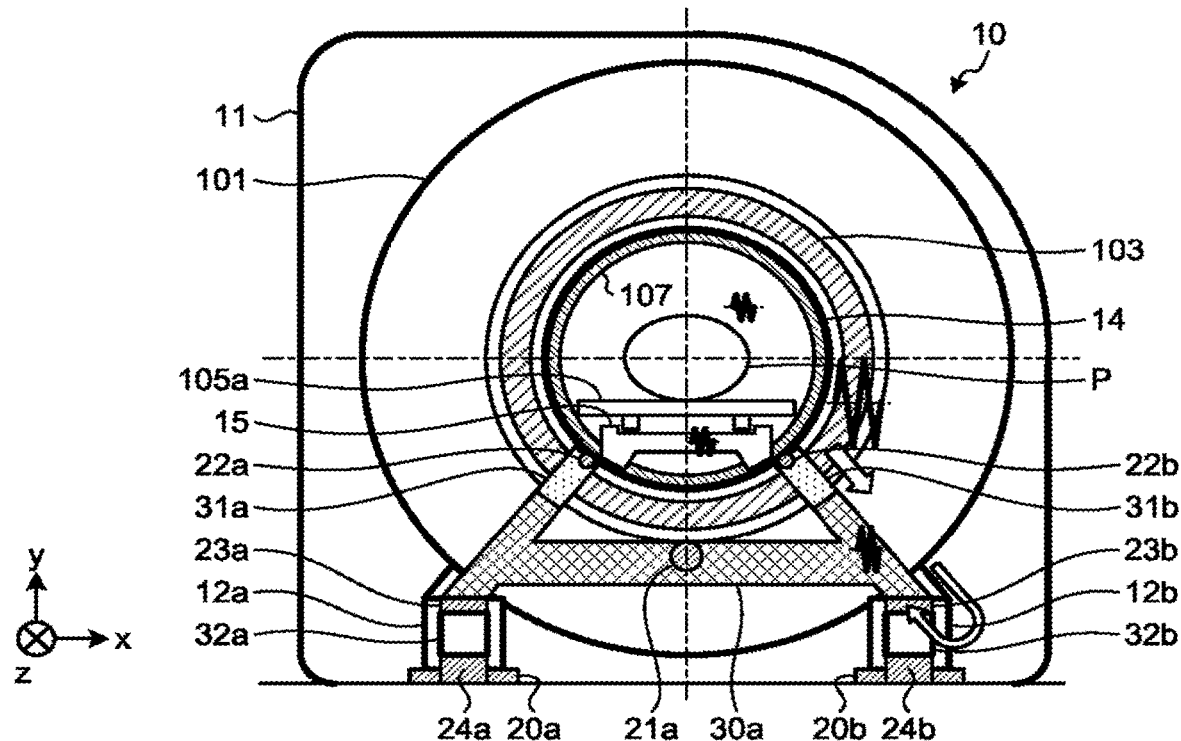
FIG. 4 is a diagram for explaining an effect caused by the MRI apparatus according to the embodiment.
Figure 5:
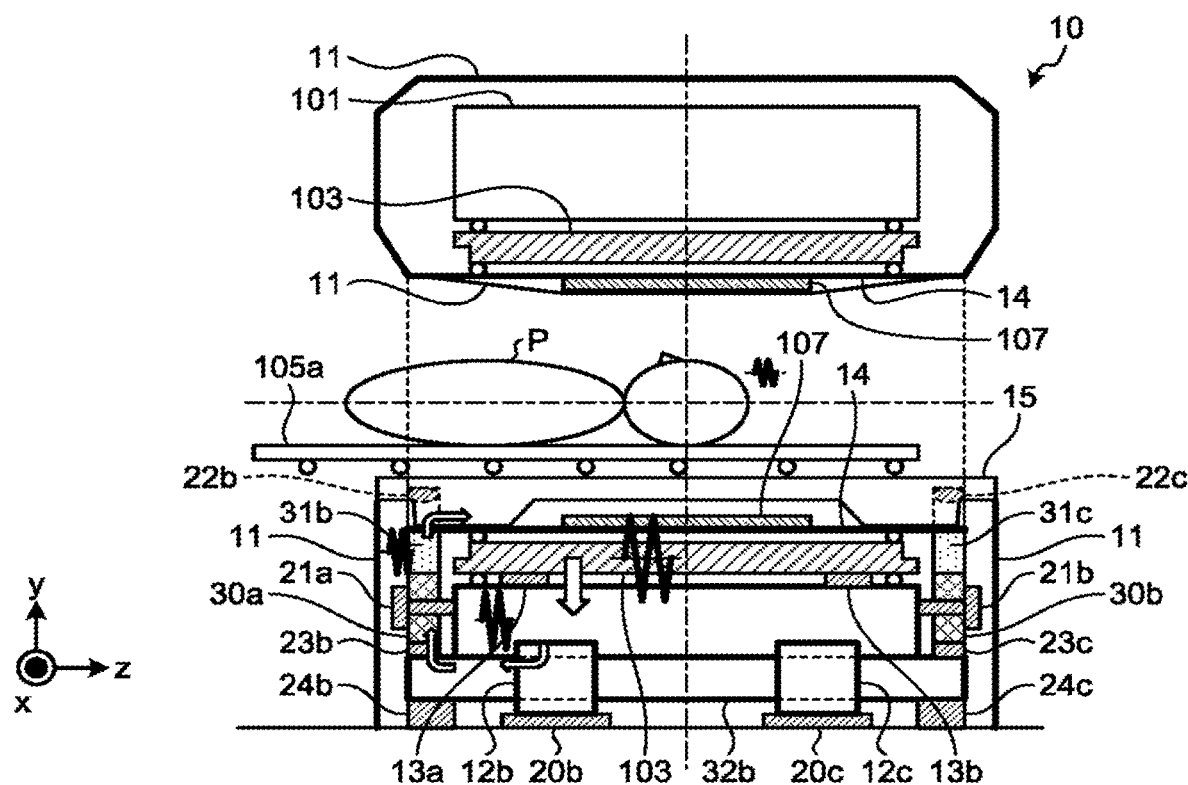
FIG. 5 is a diagram for explaining the effect caused by the MRI apparatus according to the embodiment.
Figure 6:
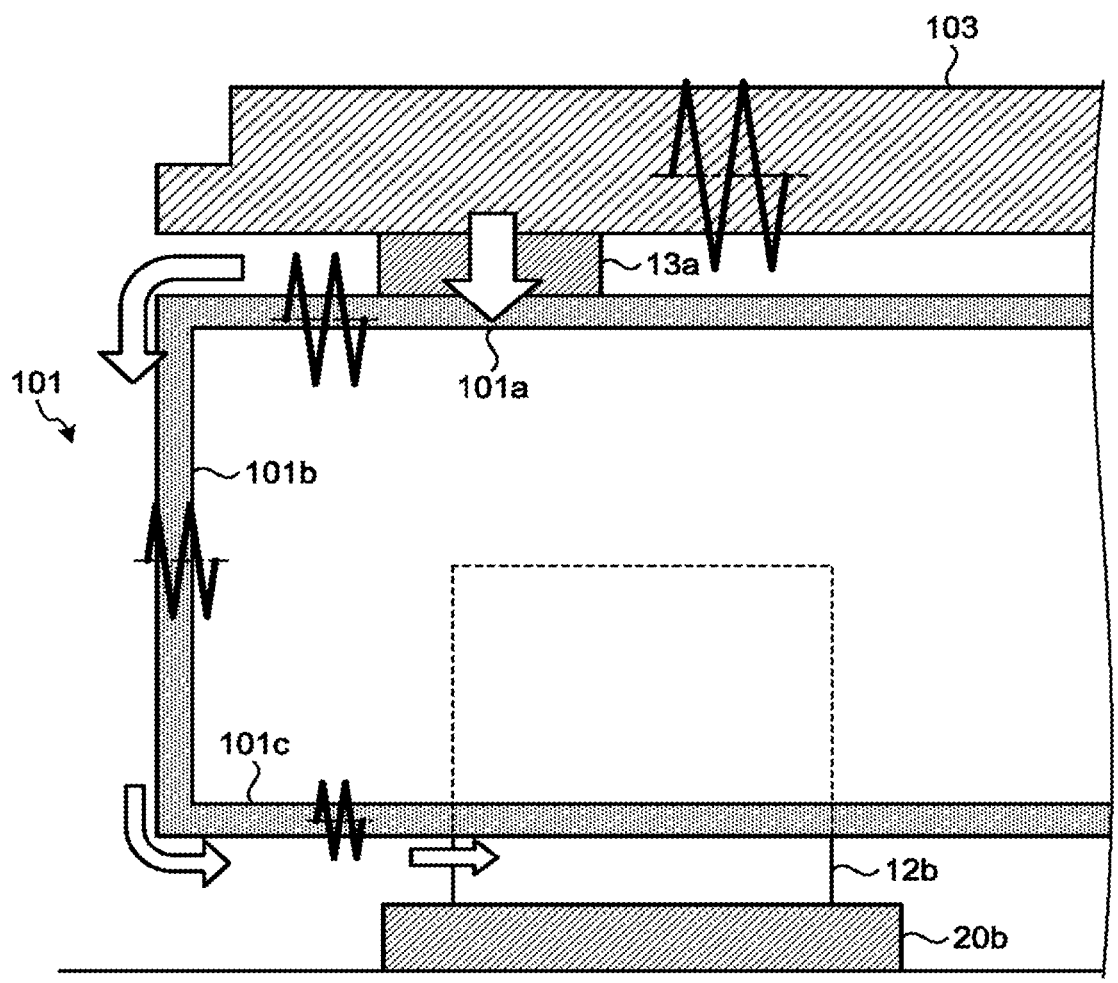
FIG. 6 is a diagram for explaining the effect caused by the MRI apparatus according to the embodiment.

FIGS. 4 to 6 are diagrams for explaining the effect caused by the MRI apparatus 100 according to the embodiment. FIG. 4 exemplifies a diagram of the internal structure of the gantry 10 viewed from its axial direction. FIG. 5 exemplifies a cross sectional view along the y-z plane passing through the center axis of the static magnetic field magnet 101. FIG. 6 exemplifies an enlarged view of the static magnetic field magnet 101 exemplified in FIG. 5. The waveforms illustrated in FIGS. 4 to 6 indicate the solid propagation vibrations in the positions illustrated in FIGS. 4 to 6 and the sizes of the waveforms correspond to the magnitudes of vibrations. The arrows illustrated in FIGS. 4 to 6 indicate the directions in which the solid propagation vibrations propagate and the line thicknesses of the arrows correspond to the magnitudes of vibrations.

As illustrated in FIGS. 4 and 5, the solid propagation vibrations caused by the gradient coil 103 propagate to the magnet legs 12a to 12d via the static magnetic field magnet 101. The solid propagation vibrations are transmitted to the front frame (the supporting members 30a, 31a and 31b) and the back frame (the supporting members 30b, 31c and 31d) via the bottom frame (supporting members 32a and 32b) supported by the magnet legs 12a to 12d and propagate to the bore tube 14 eventually. In other words, in the MRI apparatus 100, the propagation route from the gradient coil 103 to the magnet legs 12a to 12d and the propagation route from the magnet legs 12a to 12d to the bore tube 14 are configured such that the propagation routes do not intersect and accordingly the solid propagation vibrations caused by the gradient coil 103 are via the magnet legs 12a to 12d. Accordingly, the propagation route of the solid propagation vibrations is long compared to, for example, the case where the solid propagation vibrations propagate not via the magnet legs 12a to 12d and thus the MRI apparatus 100 according to the embodiment is able to reduce the solid propagation vibrations caused by the gradient coil 103. Specifically, the solid propagation vibrations caused by the gradient coil 103 propagate to the static magnetic field magnet 101, the magnet legs 12a to 12d, the bottom frame, the front frame (or the back frame) and the bore tube 14 according to the order in which they appear in this sentence and accordingly attenuate according to the propagation distance (refer to the waveforms and arrows in FIGS. 4 and 5).

The magnet legs 12a to 12d are characterized in that, as the magnet legs 12a to 12d support the weight of the static magnetic field magnet 101 and the structure mounted on the gantry 10, the rigidity of the magnet legs 12a to 12d is significantly high among the components of the MRI apparatus 100. Furthermore, as the magnet legs 12a to 12d contact the floor surface, it is possible to disperse the vibration energy to the floor surface. Accordingly, the solid propagation vibrations propagated to the magnet legs 12a to 12d are attenuated because of the rigidity of the magnet legs 12a to 12d and the dispersion of the vibration energy to the floor surface.

Furthermore, as illustrated in FIG. 6, the static magnetic field magnet 101 is formed of a plate member 101a that forms the inner circumferential surface of the static magnetic field magnet 101, a plate member 101b that forms an end face, and a plate member 101c that forms the outer circumferential surface. The static magnetic field magnet 101 is a structure in which a superconducting coil is housed.

For this reason, the solid propagation vibrations having propagated to the static magnetic field magnet 101 propagate to the plate member 101a, the plate member 101b, and the plate member 101c according to the order in which they appear in this sentence. In other words, the solid propagation vibrations having propagated to the static magnetic field magnet 101 do not linearly propagate through the static magnetic field magnet 101 toward the magnet legs 12a to 12d but propagate around the surface of the static magnetic field magnet 101. As described above, the MRI apparatus 100 according to the embodiment is able to reduce the solid propagation vibrations by using the distance on the surface of the static magnetic field magnet 101.

As described above, according to the MRI apparatus 100 according to the embodiment, extending the propagation route of the solid propagation vibrations caused by the gradient coil 103 enables attenuation according to the length of the propagation route. As a result, the MRI apparatus 100 is able to reduce the solid propagation sound caused by the gradient coil 103.

FIGS. 2 and 3 illustrate that the supporting members 30a and 30b are attached to the end faces of the static magnetic field magnet 101 via the vibration absorbing members 21a and 21b, respectively, and this is for inhibiting the motion (sway) of the bore tube 14 (and the WB coil 107) in its axial direction (z-direction). In other words, the weight of the bore tube 14 and the weight applied to the bore tube 14 (the weight of the couch rail 15 and the weight of the subject P) are supported by the supporting members 32a and 32b. In other words, the MRI apparatus 100 is able to use, for the vibration absorbing members 21a and 21b, a vibration absorbing material that is soft compared to the case where the vibration absorbing members 21a and 21b are attached to the end faces of the static magnetic field magnet 101 in order to support the weight of the bore tube 14 and the weight applied to the bore tube 14. The MRI apparatus 100 is thus able to attenuate the solid propagation vibrations transmitted from the end faces of the static magnetic field magnet 101 to the supporting members 30a and 30b via the vibration absorbing members 21a and 21b.

According to FIGS. 2 and 3, the couch rail 15 is supported by the bore tube 14. This allows lowering the rigidity of the couch rail 15 compared to the case where the couch rail 15 is not supported by the bore tube 14 and both ends of the couch rail 15 are supported by supporting members (for example, the front frame and the back frame). As a result, the MRI apparatus 100 enables lowering the weight and cost of the couch rail 15.

According to FIGS. 2 and 3, the weight of the bore tube 14 and the weight applied to the bore tube 14 are supported by the bore tube supporting structure. For this reason, the weight of the bore tube 14 and the weight applied to the bore tube 14 are not applied to the gradient coil 103 and therefore it is possible to also use a noise reduction technology of sealing the ends of the gradient coil 103 with relatively soft vacuum sealing members.

The content illustrated in FIGS. 2 to 6 is an example only and the embodiments are not necessarily limited to the configuration illustrated in the drawings. For example, the above-described example illustrates the case where each of the supporting members 32a and 32b is a member longer than the length of the static magnetic field magnet 101 in its axial direction; however, the embodiments are not limited thereto. For example, each of the supporting members 32a and 32b may be divided approximately at the center in its axial direction and the divided parts support the front frame and the back frame individually; however, as illustrated in the drawings, the structure in which each of the supporting members 32a and 32b is continuous in their axial direction has higher rigidity and is useful in supporting the weight of the bore tube 14 and the weight applied to the bore tube 14.

The above-described example illustrates the front frame and the back frame separately for the purpose of illustration; however, the embodiments are not limited thereto. For example, when the front frame and the back frame consist of the same member, the front frame and the back frame do not have to be separated.

The above-described example further illustrates the case where each of the front frame and the back frame is formed of the three members (the supporting members 30a, 31a and 31b for the front frame); however, the embodiments are not limited thereto and any number of members may be combined to configure each of the front frame and the back frame.

The above-described embodiment illustrates the case where the bore tube 14 is directly supported by the bore tube support structure; however, the embodiments are not limited thereto. For example, the bore tube 14 may be supported by the bore tube supporting structure indirectly. For example, the bore tube 14 is supportable by the bore tube supporting structure indirectly via the couch rail 15. Specifically, the bore tube supporting structure supports the couch rail 15 and the couch rail 15 supports the bore tube 14. In this case, the couch rail 15 has rigidity enabling supporting the weight of the bore tube 14 and the weight applied to the bore tube 14.

Other Embodiments

The embodiment has been described above, and various embodiments other than the above-described embodiment may be carried out.

Supporting Motion in Axial Direction on One Side

For example, the above-described embodiment (FIGS. 2 and 3) illustrates the case where the static magnetic field magnet 101 is supported from both sides in its axial direction in order to inhibit the motion of the bore tube 14 in its axial direction; however, the embodiments are not limited thereto. For example, the motion of the bore tube 14 in its axial direction is supportable from one side of the static magnetic field magnet 101 in its axial direction.

Figure 7:
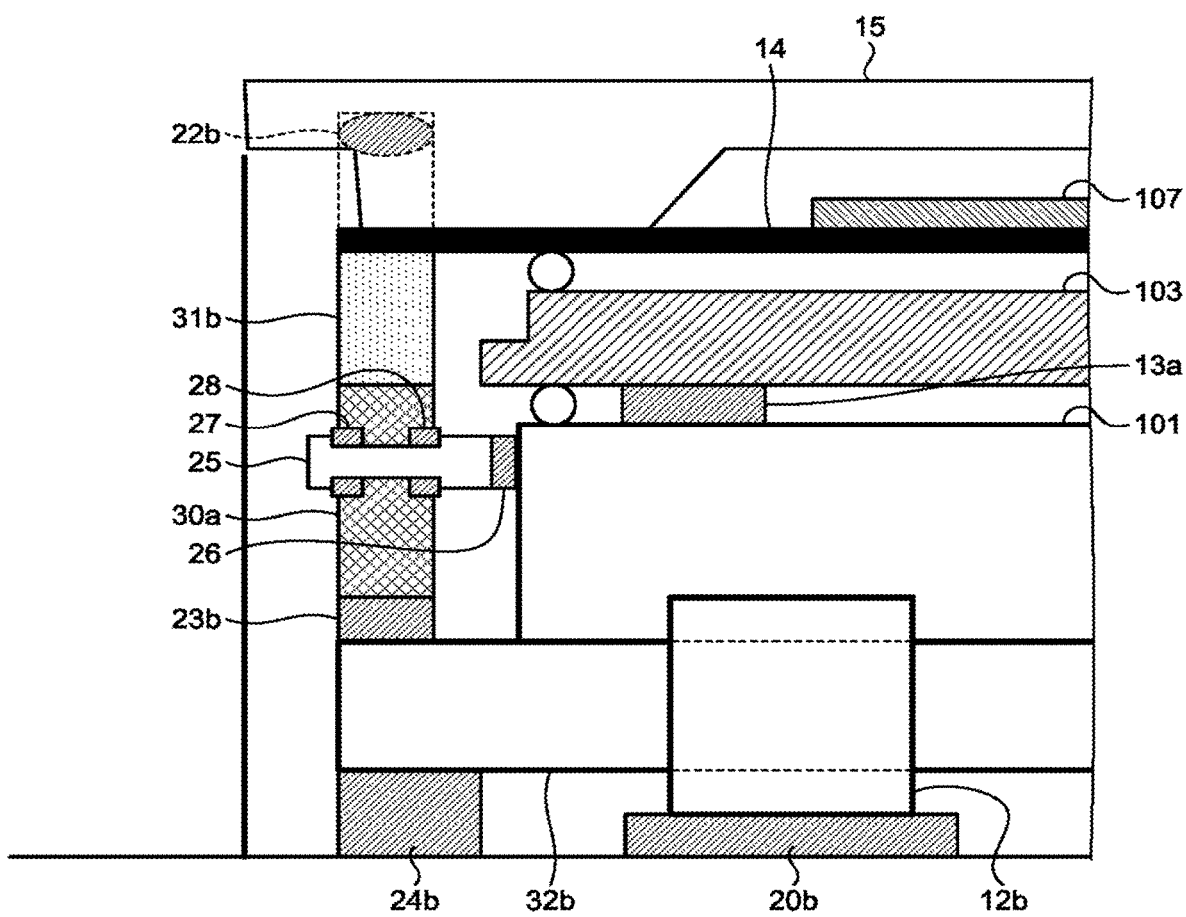
FIG. 7 is a diagram for explaining a configuration of a gantry of an MRI apparatus according to another embodiment.

FIG. 7 is a diagram for explaining a configuration of the gantry 10 of the MRI apparatus 100 according to another embodiment. FIG. 7 exemplifies a cross sectional view along a y-z plane passing through the center axis of the static magnetic field magnet 101. The example according to FIG. 7 illustrates the case where the supporting member 30a is attached to an end face of the static magnetic field magnet 101 (the end face on the side of the couch). Alternatively, the supporting member 30b may be attached to the other end face of the static magnetic field magnet 101 (the end face on the counter side of the couch).

As illustrated in FIG. 7, the supporting member 30a is attached to the end face of the static magnetic field magnet 101 on the side of the couch with a shoulder bolt 25. One end of the shoulder bolt 25 is attached to the end face of the static magnetic field magnet 101 via a vibration absorbing member 26. The shoulder bolt 25 is attached to the supporting member 30a via a vibration absorbing member 27 and a vibration absorbing member 28.

The vibration absorbing member 27 inhibits the motion in the positive direction of the z-direction. The vibration absorbing member 28 further inhibits the motion in the negative direction of the z-direction. Accordingly, the motion of the bore tube 14 in its axial direction is supported from one side of the static magnetic field magnet 101 in its axial direction.

Space Forming Structure

The above-described embodiment illustrates the case where the bore tube 14 is supported from the magnet legs; however, the embodiments are not limited thereto. In other words, the above-described embodiment may enable reduction of the solid propagation sound transmitted to the subject (patient) by supporting, not the bore tube 14, but a structure forming a patient space (space forming structure) from the magnet legs.

In other words, the space forming structure forms the patient space on the inner circumferential side of the gradient coil 103. In this case, the above-described bore tube supporting structure is attached to the magnet supporting members to support the space forming structure. The bore tube supporting structure is also referred to as a space forming structure supporter. The following four patterns (first to fourth patterns) to be described below are applicable to the space forming structure.

The first pattern is the case where the space forming structure is the bore tube 14 that supports the WB coil 107. This configuration is as described with reference to FIGS. 2 to 6. In the first pattern, the gantry cover 11 (the bore cover) that forms the exterior surface of the space (bore) is arranged on the inner circumferential side of the bore tube 14 and the WB coil 107 (see FIG. 3).

The second pattern is the case where the space forming structure is formed as the bore tube 14 also serving as the bore cover. In other words, the space forming structure is a bore tube that is arranged on the innermost circumferential side. The second pattern of the space forming structure will be described with reference to FIG. 8.

Figure 8:
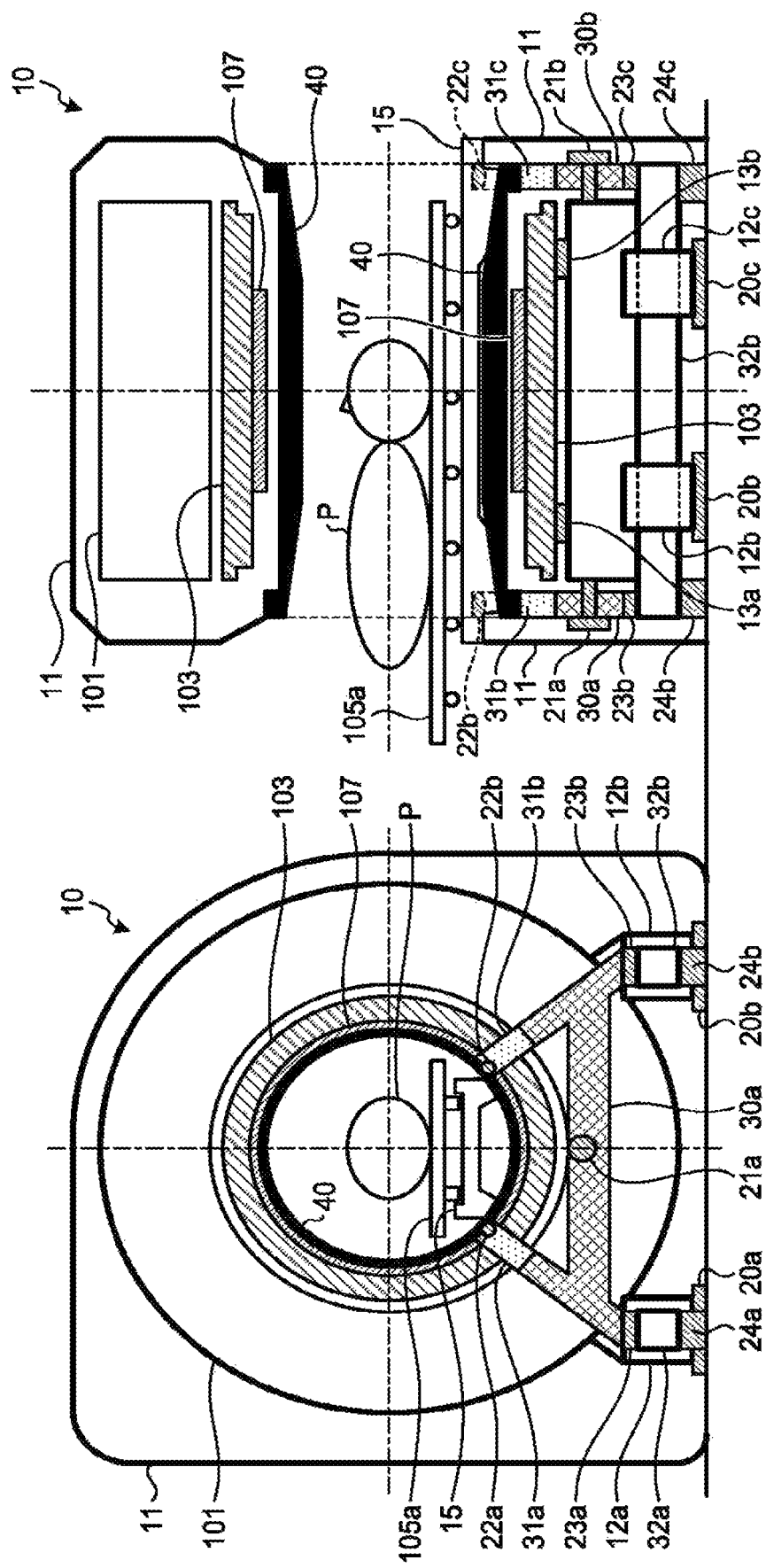
FIG. 8 is a diagram for explaining a configuration of a gantry of an MRI apparatus according to still another embodiment.

FIG. 8 is a diagram for explaining a structure of a gantry of an MRI apparatus according to still another embodiment. The left diagram in FIG. 8 exemplifies a diagram of the internal structure of the gantry 10 viewed from its axial direction. The right diagram in FIG. 8 exemplifies a cross sectional view taken along a y-z plane passing through the center axis of the static magnetic field magnet 101. The same components among those illustrated in FIG. 8 as those described with reference to FIGS. 2 and 3 will be denoted with the same reference numbers in FIGS. 2 and 3 and descriptions thereof will be omitted.

As illustrated in FIG. 8, a bore tube 40 is arranged instead of the bore tube 14 in the gantry 10. The bore tube 40 is a structure that is formed into a hollow and approximately cylindrical shape. The bore tube 40 is arranged on the innermost circumferential side of the gantry 10. The bore tube 40 has a shape connecting one end of the gantry in its axial direction and the other end and has strength enabling the shape to be maintained. The couch rail 15 is set on the inner side of the bore tube 40. The inner circumferential surface of the bore tube 40 is coated to form the exterior surface of the bore (the surface viewed by the subject).

The bore tube 40 is supported by the space forming structure originating on the magnet legs 12a to 12d. The configuration of the space forming structure supporter is the same as the configuration of the bore tube supporting structure described with reference to FIGS. 2 and 3. In other words, the front frame (the supporting member 30a, the supporting member 31a and the supporting member 31b) supports the end of the bore tube 40 at the end of the bottom frame (the supporting member 32a and the supporting member 32b) on the side of the couch. The back frame (the supporting member 30b, the supporting member 31c, and the supporting member 31d (not illustrated)) supports the end of the bore tube 40 at the end of the bottom frame on the counter side of the couch. Accordingly, the MRI apparatus 100 enables reduction of the solid propagation sound (solid propagation vibrations) caused by the gradient coil 103.

FIG. 8 illustrates the case where the WB coil 107 is supported by the gradient coil 103; however, the embodiments are not limited thereto, and the WB coil 107 may be supported by any supporting mechanism. For example, the WB coil 107 may be set on the outer circumferential surface of the bore tube 40 and thus may be supported.

The third pattern is the case where the space forming structure is formed of the couch rail and a top cover of the couch rail. The third pattern of the space forming structure will be described with referent to FIG. 9.

Figure 9:
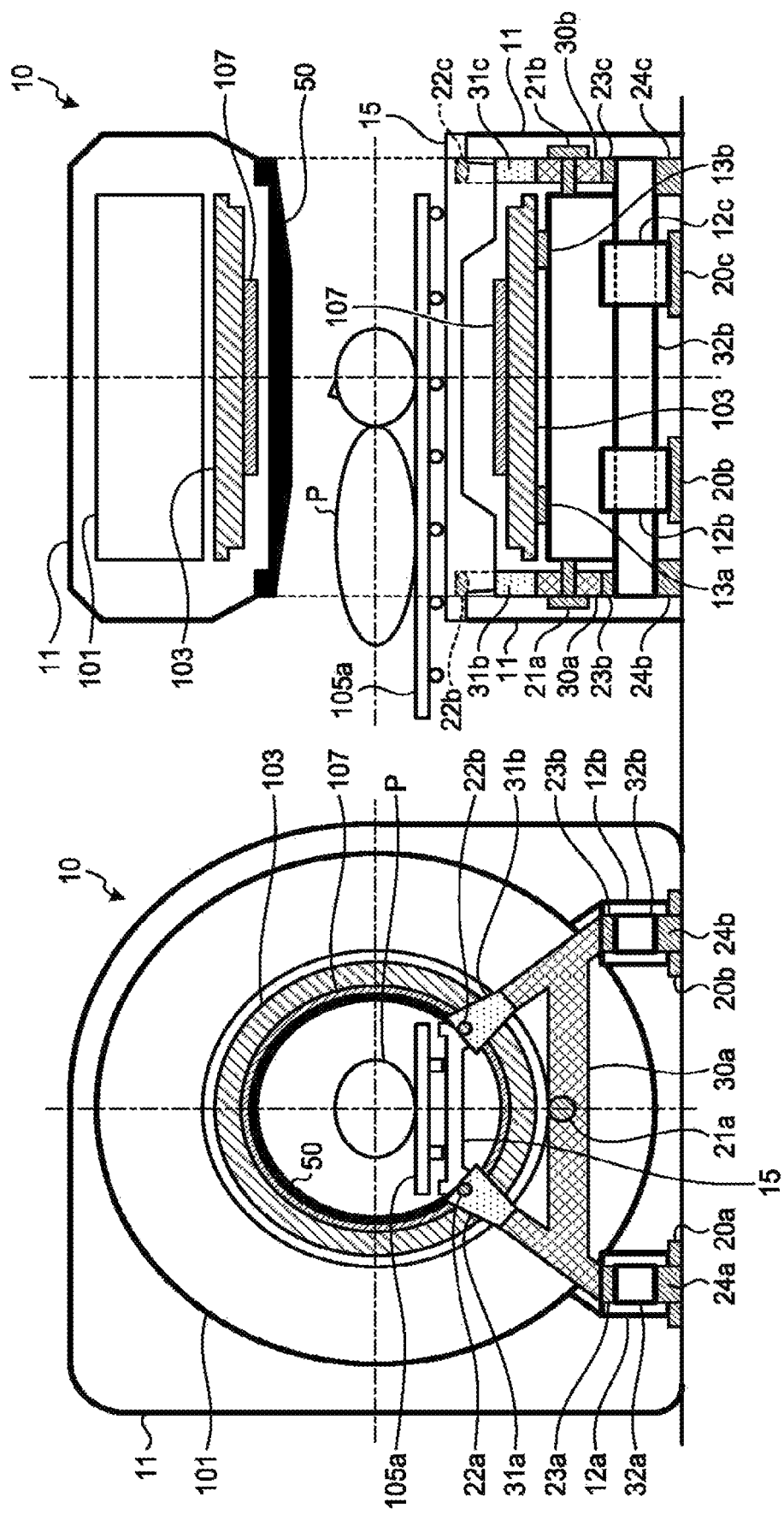
FIG. 9 is a diagram for explaining a configuration of a gantry of an MRI apparatus according to still another embodiment.

FIG. 9 is a diagram for explaining a configuration of a gantry of an MRI apparatus according to still another embodiment. The left diagram in FIG. 9 exemplifies a diagram of the internal structure of the gantry 10 viewed from its axial direction. The right diagram in FIG. 9 exemplifies a cross-sectional view along a y-z plane passing through the center axis of the static magnetic field magnet 101. The same components among those illustrated in FIG. 9 as those described with reference to FIGS. 2 and 3 will be denoted with the same reference numbers in FIGS. 2 and 3 and descriptions thereof will be omitted.

As illustrated in FIG. 9, a space forming structure that is formed of the couch rail 15 and a top cover 50 of the couch rail 15 is arranged instead of the bore tube 14 in the gantry 10. The couch rail 15 movably supports the couchtop 105a on which the subject is placed. The couch rail 15 has the same configuration as that described with reference to FIGS. 2 and 3 except that the top cover 50 is attached.

The top cover 50 is configured to cover the space above the couch rail 15 along the inner circumference of the gradient coil 103. The top cover 50 is formed of a member that is curved such that the cross section of the gantry 10 along a x-y plane has a shape of C. Arranging the top cover 50 above the couch rail 15 forms a patient space. The top cover 50 has a strength enabling the patient space to be maintained. The inner circumferential surface of the top cover 50 is coated to form the exterior surface of the bore (the surface viewed by the subject).

The space forming structure (the couch rail 15 and the top cover 50) in FIG. 9 is supported by a space forming structure supporter originating on the magnet legs 12a to 12d. The configuration of the space forming structure supporter is the same as the configuration of the bore tube supporting structure described with reference to FIGS. 2 and 3. In other words, the front frame (the supporting member 30a, the supporting member 31a and the supporting member 31b) supports the end of the space forming structure at the end of the bottom frame (the supporting member 32a and the supporting member 32b) at the side of the couch. Specifically, each of the supporting member 31a and the supporting member 31b supports the couch rail 15 and the top cover 50. The back frame (the supporting member 30b, the supporting member 31c and the supporting member 31d (not illustrated)) support the end of the space forming structure at the end of the bottom frame on the counter side of the couch. Specifically, each of the supporting member 31c and the supporting member 31d supports the couch rail 15 and the top cover 50. Accordingly, the MRI apparatus 100 is able to reduce the solid propagation sound (solid propagation vibrations) caused by the gradient coil 103.

FIG. 9 illustrates the case where the WB coil 107 is supported by the gradient coil 103; however, the embodiments are not limited thereto, and the WB coil 107 may be supported by any supporting mechanism. For example, the WB coil 107 may be set on the outer circumferential surface of the space forming structure (the couch rail 15 and the top cover 50) in FIG. 9 and thus may be supported.

The fourth pattern is the case where the space forming structure is formed of a coil structure including the WB coil 107. The fourth pattern of the space forming structure will be described with reference to FIG. 10.

Figure 10:
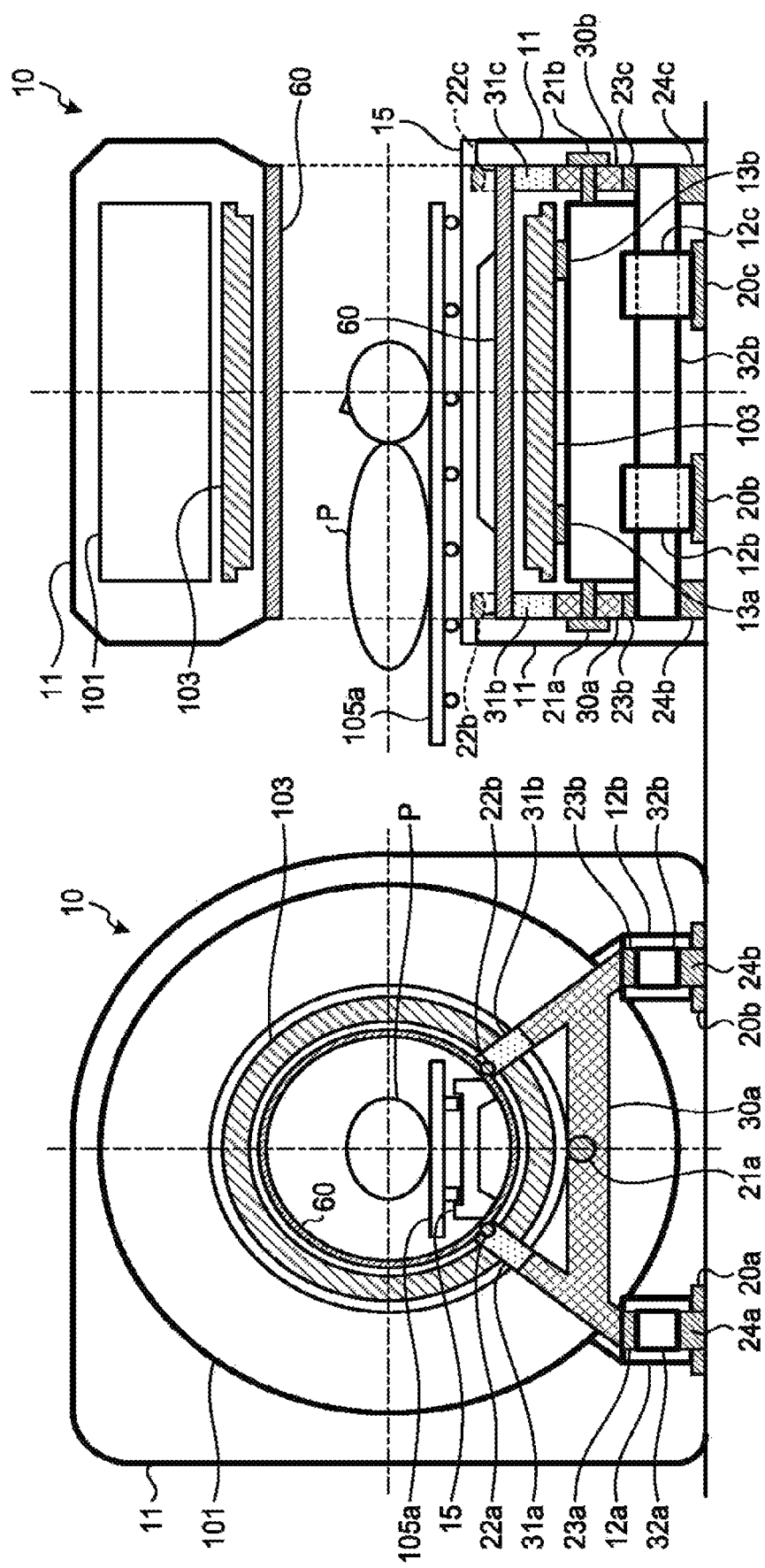
FIG. 10 is a diagram for explaining a configuration of a gantry of an MRI apparatus according to still another embodiment.

FIG. 10 is a diagram for explaining a configuration of a gantry of an MRI apparatus according to still another embodiment. The left diagram in FIG. 10 exemplifies a diagram of the internal structure of the gantry 10 viewed from its axial direction. The right diagram in FIG. 10 exemplifies a cross-sectional view along a y-z plane passing through the center axis of the static magnetic field magnet 101. The same components among those illustrated in FIG. 10 as those described with reference to FIGS. 2 and 3 will be denoted with the same reference numbers in FIGS. 2 and 3 and descriptions thereof will be omitted.

As illustrated in FIG. 10, a coil structure 60 is arranged instead of the bore tube 14 in the gantry 10. For example, the coil structure 60 is formed by being impregnated with a conductive pattern of the WB coil 107. The coil structure 60 is a structure that is formed into a hollow and approximately cylindrical shape. The coil structure 60 has a shape connecting one end of the gantry in its axial direction to the other end and has strength enabling the shape to be maintained. The couch rail 15 is set on the inner side of the coil structure 60. The inner circumferential surface of the coil structure 60 is coated to form the exterior surface of the bore.

The coil structure 60 is supported by the space forming structure supporter originating on the magnet legs 12a to 12d. The configuration of the space forming structure supporter is the same as that of the bore tube supporting structure described with reference to FIGS. 2 and 3. In other words, the front frame (the supporting member 30a, the supporting member 31a and the supporting member 31b) supports the end of the coil structure 60 at the end of the bottom frame (the supporting member 32a and the supporting member 32b) on the side of the couch. The back frame (the supporting member 30b, the supporting member 31c and the supporting member 31d (not illustrated in the drawings)) supports the end of the coil structure 60 at the end of the bottom frame on the counter side of the couch. Accordingly, the MRI apparatus 100 is able to reduce the solid propagation sound (solid propagation vibrations) caused by the gradient coil 103.

FIG. 10 illustrates the configuration in which the coil structure 60 also serves as a bore cover; however, the embodiments are not limited thereto, and a bore cover may be arranged as another structure on the inner circumferential side of the coil structure 60.

Configuration of Couch Rail

The content illustrated in FIGS. 8 to 10 is an example only and the embodiments are not limited to the example illustrated in the drawings. For example, components among the components illustrated in FIGS. 8 to 10 other than the components relating to the space forming structure may be changed optionally.

Configuration of Couch Rail

The structure of the couch rail 15 exemplified in the above-described embodiment is an example only and the embodiments are not limited thereto. For example, the couch rail may consist of two members.

Figure 11:
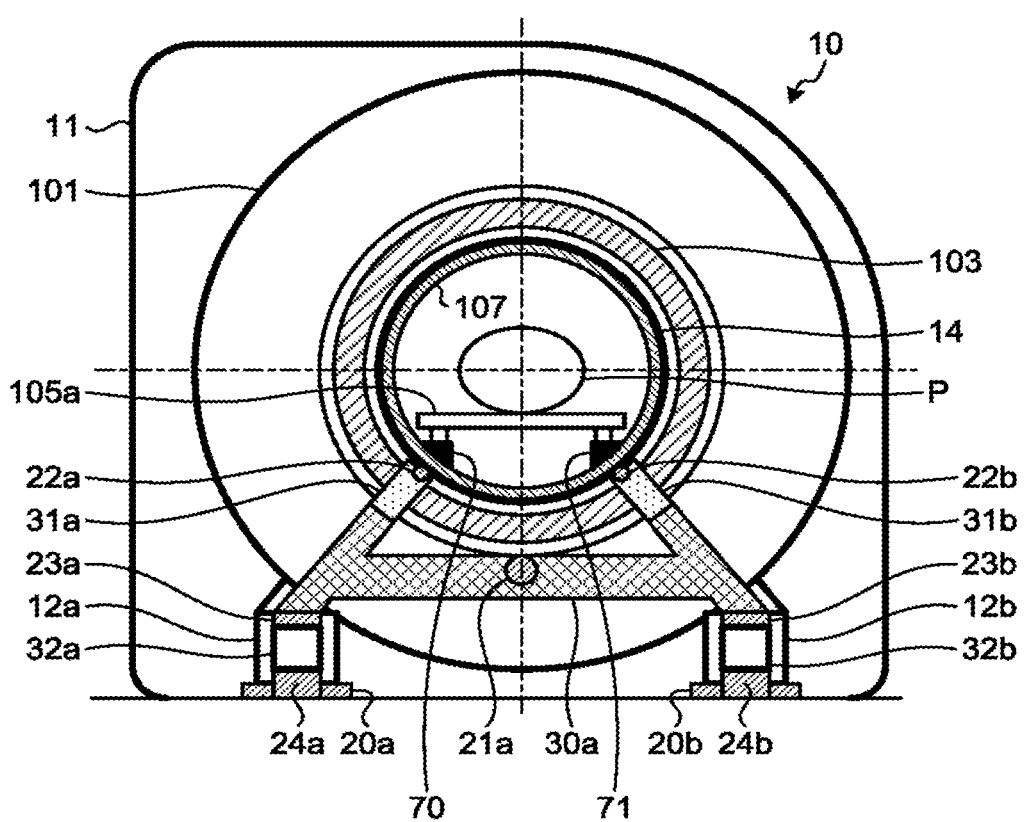
FIG. 11 is a diagram for explaining a configuration of a couch rail according to still another embodiment.

FIG. 11 is a diagram for explaining a configuration of a couch rail according to still another embodiment. FIG. 11 exemplifies a diagram of the internal structure of the gantry 10 viewed from its axial direction. The same components among those illustrated in FIG. 11 as those described with reference to FIG. 2 will be denoted with the same reference numbers in FIG. 2 and descriptions thereof will be omitted.

As illustrated in FIG. 11, two couch rails 70 and 71 are set on the gantry 10. Each of the couch rails 70 and 71 is a bar member extending in its axial direction and movably supports the couchtop 105a. The couch rails 70 and 71 are applicable to the first, second and fourth patterns among the above-described four patterns of the space forming structure.

According to at least one of the embodiments, it is possible to reduce solid propagation sound caused by the gradient coil.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
   a static magnetic field magnet;
   a gradient coil that is provided on an inner circumferential side of the static magnetic field magnet;
   a space forming structure forming a patient space on an inner circumferential side of the gradient coil;
   a magnet supporting member supporting the static magnetic field magnet on a floor surface; and
   a space forming structure supporter supporting the space forming structure,
   wherein the space forming structure supporter is provided on a route of propagation, the route of propagation propagating solid propagation vibrations from the gradient coil to the space forming structure via the magnet supporting member.

2. The magnetic resonance imaging apparatus according to claim 1, wherein the space forming structure is a bore tube that supports a whole body (WB) coil.

3. The magnetic resonance imaging apparatus according to claim 1, wherein the space forming structure is a bore tube that is arranged on an innermost circumferential side.

4. The magnetic resonance imaging apparatus according to claim 1, wherein the space forming structure is formed of a couch rail movably supporting a couchtop on which a subject is placed and a top cover covering a space above the couch rail along an inner circumference of the gradient coil.

5. The magnetic resonance imaging apparatus according to claim 1, wherein the space forming structure is a coil structure including a whole body (WB) coil.

6. The magnetic resonance imaging apparatus according to claim 1, wherein the gradient coil is supported by a coil supporting member that is provided between the inner circumferential side of the static magnetic field magnet and an outer circumferential side of the gradient coil.

7. The magnetic resonance imaging apparatus according to claim 1, wherein the space forming structure supporter includes
   a first supporting member extending in an axial direction of the static magnetic field magnet and supported by the magnet supporting member; and
   a second supporting member connecting the space forming structure and the first supporting member at an end face of the static magnetic field magnet in the axial direction.

8. The magnetic resonance imaging apparatus according to claim 7, wherein
   at least the magnet supporting member is arranged in each of two spaces that are spaces between the static magnetic field magnet and the floor surface and that are sectioned along a perpendicular plane passing through the axial direction of the static magnetic field magnet, and
   the first supporting member is supported such that the first supporting member penetrates through the magnet supporting member in the axial direction.

9. The magnetic resonance imaging apparatus according to claim 7, wherein the first supporting member is formed to be hollow.

10. The magnetic resonance imaging apparatus according to claim 7, wherein the second supporting member is formed of multiple members each of which is adhered with an elastic adhesive.

11. The magnetic resonance imaging apparatus according to claim 10, wherein a member corresponding to an inner area of the static magnetic field magnet among the multiple members forming the second supporting member is formed of a material having a property of at least one of non-conductivity and non-magnetism.

12. The magnetic resonance imaging apparatus according to claim 7, wherein the second supporting member is formed to be hollow and the hollow area is filled with a vibration-absorbing gel material.

13. The magnetic resonance imaging apparatus according to claim 7, wherein the first supporting member supports the second supporting member via a first vibration absorbing member.

14. The magnetic resonance imaging apparatus according to claim 13, wherein, when the first vibration absorbing member is arranged at each of both ends of the first supporting member in an axial direction of the first supporting member, the first vibration absorbing members arranged on both sides are respectively formed of vibration absorbing materials having different spring constants.

15. The magnetic resonance imaging apparatus according to claim 7, wherein the second supporting member is attached to an end face of the static magnetic field magnet via a second vibration absorbing member.

16. The magnetic resonance imaging apparatus according to claim 15, wherein the second vibration absorbing member is formed of a vibration mitigation alloy.

17. The magnetic resonance imaging apparatus according to claim 7, wherein
a third vibration absorbing member is arranged between one end of the first supporting member in an axial direction of the first supporting member and a floor surface, and
a fourth vibration absorbing member is arranged between the other end of the first supporting member in the axial direction of the first supporting member and the floor surface.

18. The magnetic resonance imaging apparatus according to claim 17, wherein the third vibration absorbing member is formed of a vibration absorbing material having a spring constant different from that of the forth vibration absorbing member.

19. A magnetic resonance imaging apparatus comprising:
a static magnetic field magnet;
a gradient coil that is provided on an inner circumferential side of the static magnetic field magnet;
a space forming structure forming a patient space on an inner circumferential side of the gradient coil;
a magnet supporting member supporting the static magnetic field magnet on a floor surface; and
a space forming structure supporter attached to the magnet supporting member and supporting the space forming structure,
wherein the space forming structure supporter includes
a first supporting member extending in an axial direction of the static magnetic field magnet and supported by the magnet supporting member; and
a second supporting member connecting the space forming structure and the first supporting member at an end face of the static magnetic field magnet in the axial direction,
wherein the second supporting member is formed to be hollow and the hollow area is filled with a vibration-absorbing gel material.

20. A magnetic resonance imaging apparatus comprising:
a static magnetic field magnet;
a gradient coil that is provided on an inner circumferential side of the static magnetic field magnet;
a space forming structure forming a patient space on an inner circumferential side of the gradient coil;
a magnet supporting member supporting the static magnetic field magnet on a floor surface; and
a space forming structure supporter attached to the magnet supporting member and supporting the space forming structure,
wherein the space forming structure supporter includes
a first supporting member extending in an axial direction of the static magnetic field magnet and supported by the magnet supporting member; and
a second supporting member connecting the space forming structure and the first supporting member at an end face of the static magnetic field magnet in the axial direction,
wherein the first supporting member supports the second supporting member via a first vibration absorbing member.

21. A magnetic resonance imaging apparatus comprising:
a static magnetic field magnet;
a gradient coil that is provided on an inner circumferential side of the static magnetic field magnet;
a space forming structure forming a patient space on an inner circumferential side of the gradient coil;
a magnet supporting member supporting the static magnetic field magnet on a floor surface; and
a space forming structure supporter attached to the magnet supporting member and supporting the space forming structure,
wherein the space forming structure supporter includes
a first supporting member extending in an axial direction of the static magnetic field magnet and supported by the magnet supporting member; and
a second supporting member connecting the space forming structure and the first supporting member at an end face of the static magnetic field magnet in the axial direction,
wherein the second supporting member is attached to an end face of the static magnetic field magnet via a second vibration absorbing member.

22. A magnetic resonance imaging apparatus comprising:
a static magnetic field magnet;
a gradient coil that is provided on an inner circumferential side of the static magnetic field magnet;
a space forming structure forming a patient space on an inner circumferential side of the gradient coil;
a magnet supporting member supporting the static magnetic field magnet on a floor surface; and
a space forming structure supporter attached to the magnet supporting member and supporting the space forming structure,
wherein the space forming structure supporter includes
a first supporting member extending in an axial direction of the static magnetic field magnet and supported by the magnet supporting member; and
a second supporting member connecting the space forming structure and the first supporting member at an end face of the static magnetic field magnet in the axial direction, wherein
- a third vibration absorbing member is arranged between one end of the first supporting member in an axial direction of the first supporting member and a floor surface, and
- a fourth vibration absorbing member is arranged between the other end of the first supporting member in the axial direction of the first supporting member and the floor surface.

\* \* \* \* \*